United States Patent [19]
Bloomfield et al.

[11] 4,051,076
[45] Sept. 27, 1977

[54] AROMA CHEMICALS

[75] Inventors: Jordan J. Bloomfield; Dennis C. Owsley, both of St. Louis, Mo.

[73] Assignee: Monsanto Company, St. Louis, Mo.

[21] Appl. No.: 645,188

[22] Filed: Dec. 29, 1975

[51] Int. Cl.[2] .......................... C11B 9/00; C07C 13/28; C07C 45/00; C07C 49/00

[52] U.S. Cl. .................................. 252/522; 260/586 F; 260/586 G; 260/666 PY

[58] Field of Search ........ 260/586 F, 586 G, 666 PY; 252/522

[56] References Cited

U.S. PATENT DOCUMENTS

| | | | |
|---|---|---|---|
| 3,285,962 | 11/1966 | Farrissey | 260/586 F |
| 3,420,886 | 1/1969 | Erman | 260/586 F |
| 3,483,102 | 12/1969 | Arnold et al. | 260/666 PY |
| 3,925,479 | 12/1975 | Frater et al. | 252/522 |

*Primary Examiner*—Veronica O'Keefe
*Attorney, Agent, or Firm*—Howard C. Stanley

[57] ABSTRACT

Compounds represented by the structural formulae

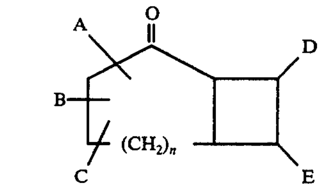

(I)

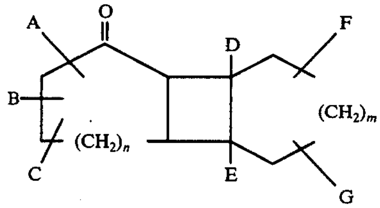

(II)

or

-continued

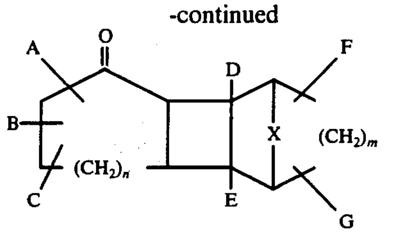

(III)

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

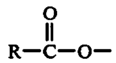

wherein R represents alkyl having from 1 to 6 carbon atoms or aryl, provided that if either D or E is alkoxy or

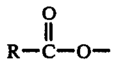

then the other substitutent D or E must be hydrogen; $m$ is an integer 1 through 8; F and G represent hydrogen or alkyl having from 1 to 3 carbon atoms; X represents

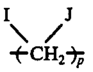

wherein $p$ is an integer 0 through 2 and I and J each independently represent hydrogen or methyl, provided that if $p$ is 0 then $m$ must be greater than 2; provided that the sum of the carbon and oxygen atoms in the compound is no greater than 23, are useful as fragrances or as components in fragrance compositions. These compounds have very pleasant, strong and long-lasting aromas. Novel compounds are also disclosed.

30 Claims, No Drawings

AROMA CHEMICALS

This invention relates to the art of fragrance compositions and, more particularly, to a class of compounds possessing desirable aromas. More specifically, this invention is directed to a class of compounds useful as fragrances or as components in fragrance compositions.

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for compounds possessing specific characteristic aromas.

The principal object of the present invention is to provide such a class of aroma chemicals.

Another object of the present invention is to provide a specific class of compounds having characteristic aromas which are useful in the preparation of fragrances and fragrance compositions.

These and other objects, aspects and advantages of this invention will become apparent from a consideration of the accompanying specification and claims.

In accordance with the above objects, there is provided by the present invention a class of compounds represented by the structural formulae

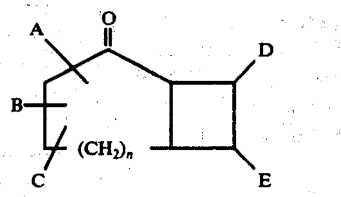

(I)

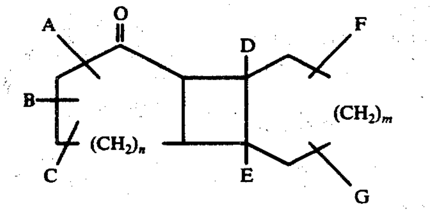

(II)

or

-continued

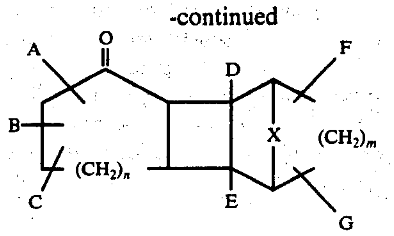

(III)

wherein *n* is an integer 0 or 1; A, B and C each independently represent hydrogen or alkyl having from 1 to 3 carbon atoms, provided that when *n* is 0 at least one of A, B and C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

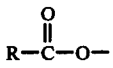

wherein R represents alkyl having from 1 to 6 carbon atoms or aryl, provided that if either D or E is alkoxy or

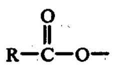

then the other substituent D or E must be hydrogen; *m* is an integer 1 through 8; F and G represent hydrogen or alkyl having from 1 to 3 carbon atoms; X represents

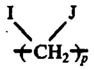

wherein *p* is an integer 0 through 2 and I and J each independently represent hydrogen or methyl, provided that if *p* is 0 then *m* must be greater than 2; provided that the sum of the carbon and oxygen atoms in the compound is no greater than 23. These compounds are useful as fragrances or as components in fragrance compositions.

Synthesis of these compounds can proceed as illustrated in the following equations:

For compounds of formula I:

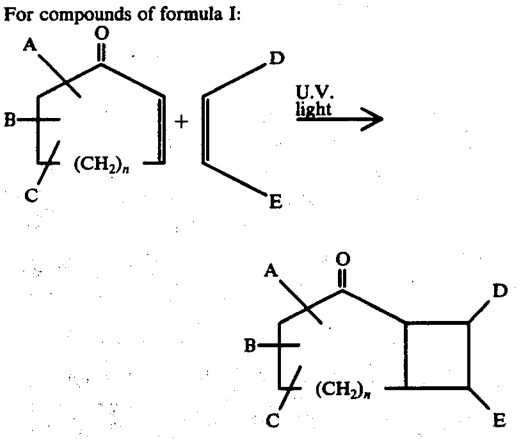

(1)

In the above equation, *n*, A, B, C, D and E have the same meanings as set forth above. As shown in equation (1) a substituted or unsubstituted cycloalkenone is reacted with an appropriate substituted or unsubstituted olefin to form the corresponding bicyclo compound. This cycloaddition is readily accomplished by conducting the reaction by irradiation of the reactants in an appropriate solvent through a glass filter which will not pass light having a wave length of less than 2600A.

For compounds of formula II:

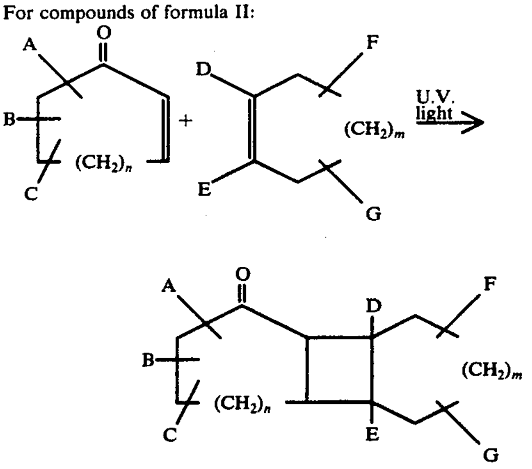

(2)

In the above equation, *n*, A, B, C, D, E, F, G and *m* have the same meanings as set forth above. As shown in equation (2), the compounds of formula II are also formed by a photosynthesis reaction of an appropriate cycloalkenone with an appropriate olefin to obtain the desired cycloaddition compounds.

For compounds of formula III:

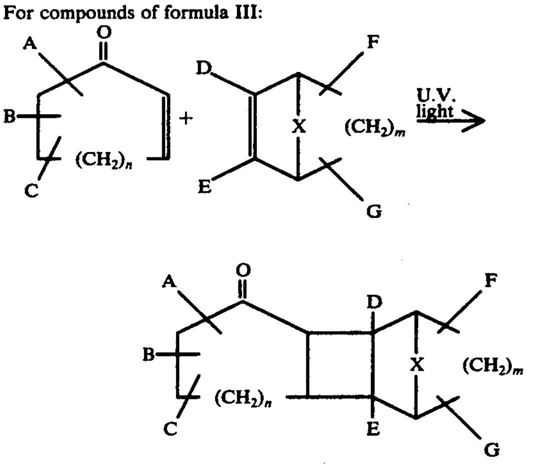

(3)

In the above equation, *n*, A, B, C, D, E, F, G, *m* and X have the same meanings as set forth above. As in the procedures for the preparation of compounds of formulae I and II, the compounds of formula III can be prepared as shown in equation (3) by a photosynthesis reaction of an appropriate cycloalkenone with an appropriate olefin to obtain the desired cycloaddition compound.

The reaction conditions are not critical but should be such as to facilitate the preparation of the products. Thus, the reaction of equations (1), (2) and (3) is normally conducted at a temperature of from low temperatures up to about 150° C. Illustrative solvents useful in these reactions are the olefins themselves, acetonitrile, benzene, acetone, ethyl acetate, hydrocarbons, ethers and methylene chloride. Methylene chloride is a preferred solvent.

More preferred embodiments are those compounds represented by the following structural formula

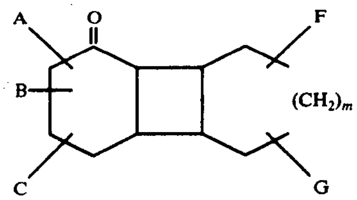

(IV)

wherein A, B, C, F, G and *m* have the same meanings as set forth above.

Still more particularly preferred compounds are represented by the following structural formulae

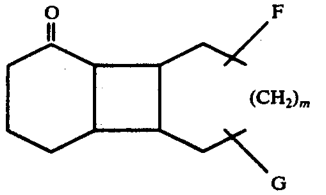

(V)

and

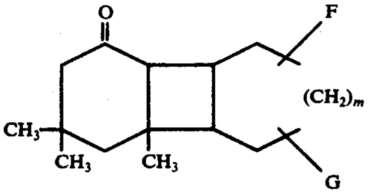

(VI)

wherein *m*, F and G have the same meanings as set forth above. The compounds of formula VI are particularly preferred novel compounds.

Compounds which exemplify this invention are 1-methyltricyclo[7.4.0.0$^{2,8}$]tridecane-10-one
1,12-dimethyltricyclo[7.4.0.0$^{2,8}$]tridecane-10-one
1,12,12-trimethyltricyclo[7.4.0.0$^{2,8}$]tridecane-10-one
1methyltricyclo[8.4.0.0$^{2,9}$]tetradecane-11-one
1,13-dimethyltricyclo[8.4.0.0$^{2,9}$]tetradecane-11-one
1-methyltricyclo[7.3.0.0$^{2,8}$]dodecane-10-one
1,12-dimethyltricyclo[7.3.0.0$^{2,8}$]dodecane-10-one
1,12,12-trimethyltricyclo[7.3.0.0$^{2,8}$]dodecane-10-one
7-methyltetracyclo[7.2.2.0$^{2,8}$0$^{3,7}$]tridecane-4-one
6,7-dimethyltetracyclo[7.2.2.0$^{2,8}$0$^{3,7}$]tridecane-4-one
6,6,7-trimethyltetracyclo[7.2.2.0$^{2,8}$0$^{3,7}$]tridecane-4-one
8-methyltetracyclo[8.2.2.0$^{2,9}$0$^{3,8}$]tetradecane-4-one
6,8-dimethyltetracyclo[8.2.2.0$^{2,9}$0$^{3,8}$]tetradecane-4-one
6,6,8-trimethyltetracyclo[8.2.2.0$^{2,9}$0$^{3,8}$]tetradecane-4-one
7-methyltetracyclo[7.2.1.0$^{2,8}$0$^{3,7}$]dodecane-4-one
6,7-dimethyltetracyclo[7.2.1.0$^{2,8}$0$^{3,7}$]dodecane-4-one
6,6,7-trimethyltetracyclo[7.2.1.0$^{2,8}$0$^{3,7}$]dodecane-4-one
8,11-(or 12-)dimethyltetracyclo[8.2.1.0$^{2,9}$0$^{3,8}$]tridecane-4-one
6,8,11-(or 12-)trimethyltetracyclo[8.2.1.0$^{2,9}$0$^{3,8}$]tridecane-4-one
6,6,8,11-(or 12-)tetramethyltetracyclo[8.2.1.0$^{2,9}$0$^{3,8}$]tridecane-4-one
1,7,12,12-tetramethyltetracyclo[7.2.1.0$^{2,8}$0$^{3,7}$]dodecane-4-one 7,9,12,12-tetramethyltetracyclo[7.2.1.0$^{2,8}$0$^{3,7}$]dodecane-4-one
1,6,7,12,12-pentamethyltetracyclo[7.2.1.0$^{2,8}$0$^{3,7}$]dodecane-4-one
6,7,9,12,12-pentamethyltetracyclo[7.2.1.0$^{2,8}$0$^{3,7}$]dodecane-4-one
1,6,6,7,12,12-hexamethyltetracyclo[7.2.1.0$^{2,8}$0$^{3,7}$]dodecane-4-one
6,6,7,9,12,12-hexamethyltetracyclo[7.2.1.0$^{2,8}$0$^{3,7}$]dodecane-4-one
1,13,13-trimethyltetracyclo[8.2.1.0$^{2,9}$0$^{3,8}$]tridecane-4-one
10,13,13-trimethyltetracyclo[8.2.1.0$^{2,9}$0$^{3,8}$]tridecane-4-one
1,8,13,13-tetramethyltetracyclo[8.2.1.0$^{2,9}$0$^{3,8}$]tridecane-4-one
8,10,13,13-tetramethyltetracyclo[8.2.1.0$^{2,9}$0$^{3,8}$]tridecane-4-one
1,6,8,13,13-pentamethyltetracyclo[8.2.1.0$^{2,9}$0$^{3,8}$]tridecane-4-one
6,8,10,13,13-pentamethyltetracyclo[8.2.1.0$^{2,9}$0$^{3,8}$]tridecane-4-one
1,6,6,8,13,13-hexamethyltetracyclo[8.2.1.0$^{2,9}$0$^{3,8}$]tridecane-4-one
6,6,8,10,13,13-hexamethyltetracyclo[8.2.1.0$^{2,9}$0$^{3,8}$]tridecane-4-one
4-(or 5-)t-butyl-1-methyltricyclo[6.3.0.0$^{2,7}$]undecane-9-one
4-(or 5-)t-butyl-1,11-dimethyltricyclo[6.3.0.0$^{2,7}$]undecane-9-one
4-(or 5-)t-butyl-1,11,11-trimethyltricyclo[6.3.0.0$^{2,7}$]undecane-9-one
10-(or 11-)t-butyltricyclo[6.4.0.0$^{2,7}$]dodecane-3-one
10-(or 11-)t-butyl-7-methyltricyclo[6.4.0.0$^{2,7}$]dodecane-3-one
10-(or 11-)t-butyl-5,7-dimethyltricyclo[6.4.0.0$^{2,7}$]dodecane-3-one
10-(or 11-)t-butyl-5,5,7-trimethyltricyclo[6.4.0.0$^{2,7}$]dodecane-3-one
7-t-butyl-5-methylbicyclo[3.2.0]heptane-2-one
7-t-butyl-4,5-dimethylbicyclo[3.2.0]heptane-2-one
7-t-butyl-4,4,5-trimethylbicyclo[3.2.0]heptane-2-one
1-methyltricyclo[9.3.0.0$^{2,10}$]tetradecane-12-one
1,14-dimethyltricyclo[9.3.0.0$^{2,10}$]tetradecane-12-one
1,14,14-trimethyltricyclo[9.3.0.0$^{2,10}$]tetradecane-12-one
1-methyltricyclo[10.3.0.0$^{2,11}$]pentadecane-13-one
1,15-dimethyltricyclo[10.3.0.0$^{2,11}$]pentadecane-13-one
1,15,15-trimethyltricyclo[10.3.0.0$^{2,11}$]pentadecane-13-one
tricyclo[9.4.0.0$^{2,10}$]pentadecane-12-one
1-methyltricyclo[9.4.0.0$^{2,10}$]pentadecane-12-one
1,14-dimethyltricyclo[9.4.0.0$^{2,10}$]pentadecane-12-one
1,14,14-trimethyltricyclo[9.4.0.0$^{2,10}$]pentadecane-12-one
tricyclo[10.4.0.0$^{2,11}$]hexadecane-13-one
1-methyltricyclo[10.4.0.0$^{2,11}$]hexadecane-13-one
1,15-dimethyltricyclo[10.4.0.0$^{2,11}$]hexadecane-13-one
1,15,15-trimethyltricyclo[10.4.0.0$^{2,11}$]hexadecane-13-one
tricyclo[6.3.0.0$^{2,7}$]undecane-3-one
7-methyltricyclo[6.3.0.0$^{2,7}$]undecane-3-one
5,7-dimethyltricyclo[6.3.0.0$^{2,7}$]undecane-3-one
5,5,7-trimethyltricyclo[6.3.0.0$^{2,7}$]undecane-3-one
6-methyltricyclo[5.3.0.0$^{2,6}$]decane-3-one
5,6-dimethyltricyclo[5.3.0.0$^{2,6}$]decane-3-one
5,5,6-trimethyltricyclo[5.3.0.0$^{2,6}$]decane-3-one
1-methyltricyclo[6.3.0.0$^{2,7}$]undecane-9-one
1,11-dimethyltricyclo[6.3.0.0$^{2,7}$]undecane-9-one
1,11,11-trimethyltricyclo[6.3.0.0$^{2,7}$]undecane-9-one
6-ethoxy-5-methylbicyclo[3.2.0]heptane-2-one
6-ethoxy-4,5-dimethylbicyclo[3.2.0]heptane-2-one
6-ethoxy-4,4,5-trimethylbicyclo[3.2.0]heptane-2-one
7-ethoxy-6-methylbicyclo[4.2.0]octane-2-one
7-ethoxy-4,6-dimethylbicyclo[4.2.0]octane-2-one
7-ethoxy-4,4,6-trimethylbicyclo[4.2.0]octane-2-one
6-acetoxy-5-methylbicyclo[3.2.0]heptane-2-one
6-acetoxy-4,5-dimethylbicyclo[3.2.0]heptane-2-one
6-acetoxy-4,4,5-trimethylbicyclo[3.2.0]heptane-2-one
7-acetoxy-6-methylbicyclo[4.2.0]octane-2-one
7-acetoxy-4,6-dimethylbicyclo[4.2.0]octane-2-one
6-(or 7-)n-hexyl-5-methylbicyclo[3.2.0]heptane-2-one
6-(or 7-)n-hexyl-4,5-dimethylbicyclo[3.2.0]heptane-2-one
6-(or 7-)n-hexyl-4,4,5-trimethylbicyclo[3.2.0]heptane-2-one
7-(or 8-)n-hexylbicyclo[4.2.0]octane-2-one
7-(or 8-)n-hexyl-6-methylbicyclo[4.2.0]octane-2-one
7-(or 8-)n-hexyl-4,6-dimethylbicyclo[4.2.0]octane-2-one
7-(or 8-)n-hexyl-4,4,6-trimethylbicyclo[4.2.0]octane-2-one The compounds of this invention are useful as fragrances in the preparation and formulation of fragrance compositions such as perfumes and perfumed products due to their pleasing, strong and long-lasting aroma. Perfume compositions and the use thereof in cosmetic, detergent and bar soap formulations and the like are exemplary of the utility thereof. Likewise, these compounds can be utilized as the primary fragrance in many such compositions.

It has been determined that the structural formulae of the compounds of this invention form many different spatial configurations, i.e., mixtures of stereo isomers. These mixtures of isomers all appear to exhibit fragrance characteristics that are desired by perfumers in compounding fragrances.

The compounds of this invention are used in concentrations of from trace amounts up to about 50 percent of the fragrance composition into which they are incorporated. As will be expected, the concentration of the compound will vary depending on the particular fragrance desired in the composition and even within the same composition when compounded by different perfumers.

It has been found that the compounds of this invention possess notes with good intensity and persistence. This fragrance quality particularly adapts the compounds for incorporation into fragrance compositions and fragrance modifying compositions having a desirable aroma. It will be appreciated by those skilled in the art from the present invention that the fragrance character of the finished fragrance compositions can be tailored to specific uses, as more fully described hereinafter.

The compounds of this invention are olfactory agents and can be incorporated into a wide variety of compositions which will be enhanced by their fragrance notes. The compounds can be added to fragrance compositions in pure form or they can be added to mixtures of materials in fragrance-imparting compositions to provide a desired fragrance character to a finished fragrance material. The fragrance compositions obtained according to this invention are suitable in a wide variety of perfumed articles and can also be used to enhance, modify or reinforce natural fragrance materials. It will thus be appreciated that the compounds of this invention are useful as olfactory agents and fragrances.

The term "fragrance composition" is used herein to mean a mixture of compounds, including, for example, natural oils, synthetic oils, alcohols, aldehydes, ketones, esters, lactones, and frequently hydrocarbons which are admixed so that the combined odors of the individual components produce a pleasant or desired fragrance. Such fragrance compositions usually contain (a) the main note or the "bouquet" or foundationstone of the composition; (b) modifiers which round off and accompany the main note; (c) fixatives which include odorous substances which lend a particular note to the fragrance throughout all stages of evaporation, and substances which retard evaporation; and (d) top-notes which are usually low-boiling, fresh-smelling materials. Such fragrance compositions of this invention can be used in conjunction with carriers, vehicles, solvents, dispersants, emulsifiers, surface-active agents, aerosol propellants, and the like.

In fragrance compositions the individual components contribute their particular olfactory characteristics, but the overall effect of the fragrance composition will be the sum of the effect of each component. Thus, the compounds of this invention can be used to alter the aroma characteristics of a fragrance composition, for example, by highlighting or moderating the olfactory reaction contributed by another component of the composition.

The amount of compounds of this invention which will be effective in fragrance compositions depends on many factors, including the other components, their amounts and the effects which are desired. It has been found that fragrance compositions containing as much as 50% by weight or as little as trace amounts of mixtures of compounds of this invention, or even less can be used to impart a desirable odor to soaps, cosmetics and other products. The amount employed will depend on considerations of cost, nature of the end product, the effect desired in the finished product, and the particular fragrance sought.

The compounds disclosed herein can be used alone, in a fragrance-modifying composition, or in a fragrance composition as an olfactory component in detergents and soaps; space deodorants; perfumes; colognes; bath preparations such as bath oil, bath salts; hair preparations such as lacquers, brilliantines, pomades, and shampoos; cosmetic preparations such as creams, deodorants, hand lotions, sun screens; powders such as talcs, dusting powders, face powder and the like. When the compounds of this invention are used in perfumed articles such as the foregoing, it can be used in amounts of 0.1% or lower. Generally, it is preferred not to use more than about 10% in the finished perfumed article, since the use of too much will tend to unbalance the total aroma and will needlessly raise the cost of the article.

The following examples will serve to illustrate certain specific embodiments within the scope of this invention and are not to be construed as limiting the scope thereof.

EXAMPLE 1

7-(or 8-)acetoxy-4,4,6-trimethylbicyclo[4.2.0]octane-2-one

To a 5-liter, 3-necked flask equipped with a quartz immersion well and nitrogen bubbler was added, under nitrogen, 138 g. (1.0 mol.) of isophorone, 950 g. (11.05 mol.) of vinyl acetate and enough ethyl acetate to fill the flask. The solution was irradiated with an Hanovia 450 watt medium pressure mercury arc through a Corning 9700 glass filter for 35 hours. The solution was concentrated in vacuo and the oily product was distilled through a 25 cm. Vigreux-column to yield 164.5 g. (0.734 mol., 73% yield) of the desired product having b.p. 94°-100° C./0.46 mm. Hg. IR analysis confirms the structure of the isomers of the desired compound.

EXAMPLE 2

1,13,13-trimethyltricyclo[8.4.0.0$^{2,9}$]tetradecane-11-one

To a 5-liter flask equipped with a quartz immersion well and nitrogen bubbler was added, under nitrogen, 138 g. (1.0 mol.) of isophorone and 420 g. of freshly distilled cyclooctene. The flask was filled with dichloromethane and was bubbled with nitrogen for 1 hour. The solution was irradiated for 18.5 hours with an Hanovia 450 watt medium pressure mercury arc through a Corning 9700 glass filter. After 7 hours, an additional 82 g. of cyclooctene was added. The solution was concentrated in vacuo to obtain an oil which was distilled through a 45 cm. Vigreux-column to yield 218.4 g. (0.881 mol., 88% yield) of product, b.p. 106°-110° C./0.3 mm.Hg. The product by glpc consisted of 3 isomers in the approximate ratio of 75:12.5:12.5. IR: 1692 $cm^{-1}$ confirmed the production of the desired product.

EXAMPLE 3 tricyclo[8.4.0.0$^{2,9}$]tetradecane-11-one

A solution of 29.4 g. (0.3 mol.) of cyclohexenone and 200 ml. of cyclooctene in 2600 ml. of dichloromethane was irradiated at −65° C. in the low temperature photolysis apparatus described in *Organic Prep. Proc. Int.* 3, 61 (1971) with a 1000 watt G.E. mercury arc through a Corning 9700 glass filter for 4 hours. At the end of the photolysis the solution was concentrated in vacuo and the product was distilled through a short Vigreux-column to yield 51.8 g. (0.249 mol., 83% yield) of a mixture of four isomers having b.p. 108°-127° C./0.4 mm.Hg. IR: 1695 $cm^{-1}$ confirmed the structure.

EXAMPLE 4

8-tertbutyl-4,4,6-trimethylbicyclo[4.2.0]octane-2-one

To a photoreactor fitted with a quartz immersion well and nitrogen bubbler was added, under nitrogen, 27.6 g. (0.2 mol.) of isophorone, 84 g. (1.0 mol.) of 3,3-dimethyl-1-butene (t-butylethylene) and enough dichloromethane to fill the 600 ml. reactor. The solution was bubbled for 1 hour with nitrogen and was then irradiated for 45.5 hours through a Corning 9700 glass filter with an Hanovia 450 watt medium pressure mercury arc. The solution was concentrated in vacuo and the oily product was distilled on a 60 cm. stainless steel spinning band column to yield 13.2 g. (0.059 mol., 30% yield) of the desired product, b.p. 84°-86° C./0.65 mm.Hg. NMR: ($CCl_4$) 0.80δ (S-9H); 0.87δ (S-3H); 1.03δ (S-3H); 1.16δ (S-3H); 1.23δ-2.5δ (multiplets, 8H); IR: 1697 $cm^{-1}$.

EXAMPLE 5

5,5,7-trimethyltricyclo[6.4.0.0$^{2,7}$]dodecane-3-one

To a photoreactor fitted with a quartz immersion well and nitrogen bubbler was added, under nitrogen, 30.0 g. (0.217 mol.) of isophorone and 145 ml. of freshly distilled cyclohexene. Enough dichloromethane was added to fill the 825 ml. internal volume of the photoreactor. After the solution was bubbled with nitrogen for 1 hour, it was irradiated through a Corning 9700 glass filter for 7¼ hours with an Hanovia 450 watt medium pressure mercury arc. At the end of this period, the solution was concentrated in vacuo to yield an oil which was distilled through a short Vigreux-column. The product, which is a mixture of two major isomers in approximately a 3:1 ratio had b.p. 93°-106° C./0.2 mm.Hg. Yield 39.2 g. (0.178 mol., 82% yield). The two major isomers could be separated by distillation on a spinning band column. Isomer A: b.p. 85° C./0.1 mm.Hg. m.p. 76.6°-77.4° C., IR: 1690 $cm^{-1}$; NMR: (deuterochloroform) 1.20δ (S-3H); 1.07δ (S-3H); 0.90δ (S-3H); 1.32δ-2.70δ (complex multiplets-15H). Isomer B: b.p. 95° C./0.1 mm.Hg. IR: 1690 $cm^{-1}$, NMR: (deuterochloroform); 1.08δ, 1.05δ (2 singlets-6H); 0.90δ (S-3H) 1.18δ-2.82δ (multiplets-15H).

EXAMPLE 6

6,6,8-trimethyltetracyclo[8.2.1.$0^{2,9}0^{3,8}$]tridecane-4-one

To a Pyrex photoreactor equipped with a quartz immersion well and nitrogen bubbler was added, under nitrogen, 103.6 g. (0.75 mol.) of isophorone and 400 g. (4.25 mol) of freshly distilled bicyclo [2.2.1] hept-2-ene. The vessel was filled to its internal volume of 1200 ml. with dichloromethane. The solution was bubbled with nitrogen for 1 hour and irradiated through a Pyrex filter for 18.5 hours with an Hanovia 450 watt medium pressure mercury arc. After the lamp was turned off, the solution was concentrated in vacuo to obtain an oil which was distilled through a 90 cm. Vigreux-column to yield 143.6 g. (0.62 mol., 82%) of the desired product having b.p. 90°-94° C./0.5 mm.Hg. Glpc showed the product to be a 1:1 mixture of two main isomers (180 cm. × 0.3 cm. 1% OV-225 on Chrom G, 150° C. initially for 3 min. and then programmed 10° C./min. to 250° C.) IR: 1692 $cm^{-1}$ NMR: ($CCl_4$) singlets at 1.35δ, 1.10δ, 1.00δ, 0.92δ, 0.87δ with the singlet at 1.00δ having an integral area of 6H while the others integrated to 3H. The rest of the NMR spectrum was a set of complicated multiplets.

EXAMPLE 7

5,5,7-trimethyl-9-oxatricyclo[6.4.0.$0^{2,7}$]dodecane-3-one

To a 5-liter round bottomed flask equipped with a quartz immersion well and nitrogen bubbler was added, under nitrogen, 138 g. (1.0 mol.) of isophorone and 498 g. (5.93 mol.) of 3,4-dihydropyran. Enough dichloromethane was added to fill the flask. The solution was bubbled with nitrogen for 1.5 hours and was irradiated with a 450 watt Hanovia medium pressure mercury arc through a Corning 9700 glass filter for 20.5 hours. When the photolysis was completed, the solution was concentrated in vacuo to yield 107.9 g. (0.486 mol.) of a crystalline solid and 80.6 g. of a liquid (0.363 mol.) (Total yield 0.849 mol., 85%). The solid after sublimation and recrystallization had m.p. 111°-112.2° C. IR: 1690 $cm^{-1}$ NMR: ($CCl_4$) 0.92δ (S-3H), 1.12δ (S-3H); 1.32δ (S-3H); 1.35-2.15δ (multiplets 8H); 2.35δ (triplet-2H, J=14Hz); 2.65-2.93δ (M-1H); 3.38-4.20δ (M-2H). The liquid, which had b.p. 101° C./0.3 mm.Hg. was found by glpc to consist of a lower boiling minor component, the solid and a higher boiling product. Redistillation of this fraction gave a fraction, b.p. 85°-90° C./0.1 mm.Hg. which had a NMR ($CCl_4$) spectrum which had methyl singlets at 0.92δ, 1.03δ, 1.10δ and 1.30δ. The singlet at 1.30δ belonged to the solid component, which made up 34% of the mixture. IR: 1695 $cm^{-1}$.

EXAMPLE 8

A fragrance composition illustrative of the instant invention contains the following components:

| Component | Parts by Weight |
|---|---|
| Coumarin | 7.0 |
| Vanillin | 1.0 |
| Cedrenyl acetate | 2.0 |
| Cedarwood oil | 3.0 |
| Cinnamon leaf oil | 0.5 |
| Diphenylmethane | 1.0 |
| Eugenol, prime | 1.0 |
| Ethyl cinnamate | 1.0 |
| Hercolyn[1] D | 17.5 |
| Compound of Example 5 (Isomer mixture) | 20.0 |
| Isopropyl quinolene (10% in dipropylene glycol) | 4.0 |
| Linalool | 1.0 |
| Olibanum extract | 14.0 |
| Sandela[2] GD | 1.0 |
| Terpinyl acetate | 6.0 |
| Phenyl ethyl alcohol | 20.0 |

[1]A trademark of the Hercules Company
[2]A trademark of the Givaudan Company

This fragrance composition imparts a pleasant woody-type aroma.

EXAMPLE 9

The characteristic aromas of some of the compounds of the instant invention are as follows:

| Compound of Example | Aroma |
|---|---|
| 1 | incense, myrrh, olibanum, metallic |
| 2 | olibanum, incense, lasting |
| 3 | musty, floral |
| 4 | sweet, woody, sandalwood, faintly lasting |
| 5 | woody, olibanum, opoponax, extremely powerful after 12 hr. |
| 6 | bread dough, olibanum |
| 7* | weak to odorless, musty |

*The compound of Example 7 is exemplary of compounds of similar structure (heterocyclic) which are not as useful as the compounds of the instant invention.

While the invention has been described herein with regard to certain specific embodiments, it is not so limited. It is to be understood that variations and modifications thereof may be made by those skilled in the art without departing from the spirit and scope of the invention.

The embodiments of this invention in which a particular property or privilege is claimed are defined as follows:

1. A fragrance composition having incorporated therein an odoriferous amount of a compound represented by the structural formulae:

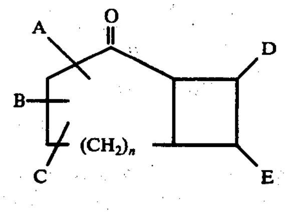

-continued

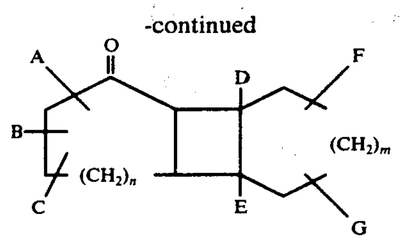

or

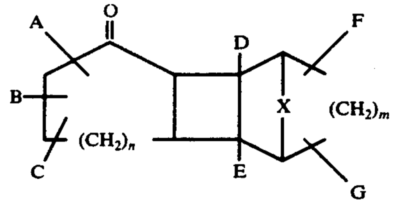

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

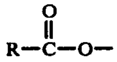

wherein R represents alkyl having from 1 to 6 carbon atoms or aryl, provided that if either D or E is alkoxy or

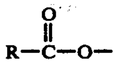

then the other substituent D or E must be hydrogen; $m$ is an integer 1 through 8; F and G represent hydrogen or alkyl having from 1 to 3 carbon atoms; X represents

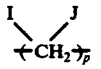

wherein $p$ is an integer 0 through 2 and I and J each independently represent hydrogen or methyl, provided that if $p$ is 0 then $m$ must be greater than 2; provided that the sum of the carbon and oxygen atoms in the compound is no greater than 23 and at least one carrier commonly used in fragrance compositions.

2. A fragrance composition as defined in claim 1 wherein the compound incorporated is represented by the structural formula

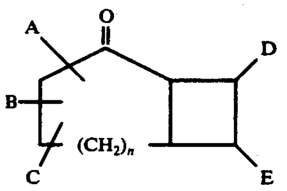

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

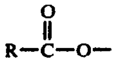

wherein R represents alkyl having from 1 to 6 carbon atoms or aryl, provided that if either D or E is alkoxy or

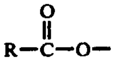

then the other substituent D or E must be hydrogen.

3. A fragrance composition as defined in claim 1 wherein the compound incorporated is represented by the structural formula

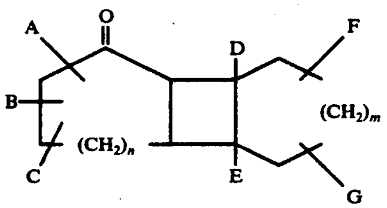

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

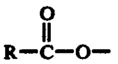

wherein R represents alkyl having from 1 to 6 carbon atoms or aryl, provided that if either D or E is alkoxy or

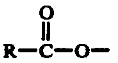

then the other substituent D or E must be hydrogen; $m$ is an integer 1 through 8; F and G represent hydrogen or alkyl having from 1 to 3 carbon atoms.

4. A fragrance composition as defined in claim 1 wherein the compound incorporated is represented by the structural formula

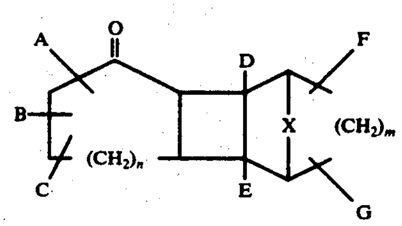

wherein *n* is an integer 0 or 1; A, B and C each independently represent hydrogen or alkyl having from 1 to 3 carbon atoms, provided that when *n* is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

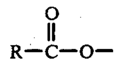

wherein R represents alkyl having from 1 to 6 carbon atoms or aryl, provided that if either D or E is alkoxy or

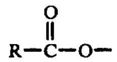

then the other substituent D or E must be hydrogen; *m* is an integer 1 through 8; F and G represent hydrogen or alkyl having from 1 to 3 carbon atoms; X represents

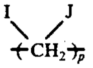

wherein *p* is an integer 0 through 2 and I and J each independently represent hydrogen or methyl, provided that if *p* is 0 then *m* must be greater than 2.

5. A fragrance composition as defined in claim 3 wherein the compound incorporated is represented by the structural formula

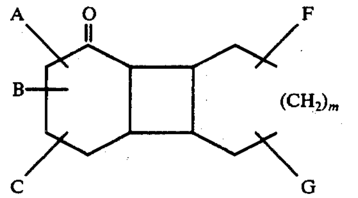

wherein A, B and C each independently represent hydrogen or alkyl having from 1 to 3 carbon atoms, *m* is an integer 1 through 8 and F and G represent hydrogen or alkyl having from 1 to 3 carbon atoms.

6. A fragrance composition as defined in claim 5 wherein the compound incorporated is represented by the structural formula

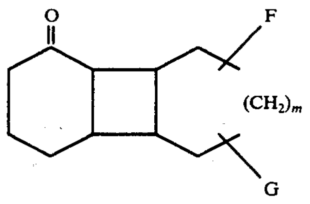

wherein *m* is an integer 1 through 8 and F and G represent hydrogen or alkyl having from 1 to 3 carbon atoms.

7. A fragrance composition as defined in claim 5 wherein the compound incorporated is represented by the structural formula

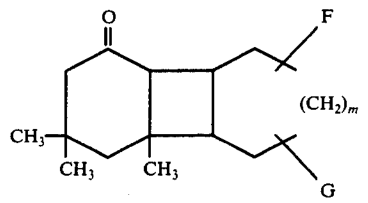

wherein *m* is an integer 1 through 8 and F and G represent hydrogen or alkyl having from 1 to 3 carbon atoms.

8. A fragrance composition as defined in claim 1 wherein the compound incorporated is 7-acetoxy-4,4,6-trimethylbicyclo[4.2.0]octane-2-one, 8-acetoxy-4,4,6-trimethylbicyclo[4.2.0]octane-2-one or mixtures thereof.

9. A fragrance composition as defined in claim 1 wherein the compound incorporated is 8-tertbutyl-4,4,6-trimethylbicyclo[4.2.0]octane-2-one.

10. A fragrance composition as defined in claim 6 wherein the compound incorporated is tricyclo[8.4.0.0$^{2,9}$]tetradecane-11-one.

11. A fragrance composition as defined in claim 7 wherein the compound incorporated is 5,5,7-trimethyltricyclo[6.4.0.0$^{2,7}$]dodecane-3-one.

12. A fragrance composition as defined in claim 7 wherein the compound incorporated is 1,13,13-trimethyltricyclo[8.4.0.0$^{2,9}$]tetradecane-11-one.

13. A fragrance composition as defined in claim 4 wherein the compound incorporated is 6,6,8-trimethyltetracyclo[8.2.1.0$^{2,9}$0$^{3,8}$]tridecane-4-one.

14. In a method of providing a fragrance, the improvement comprising the use of an odoriferous amount of a compound as represented by the structural formulae

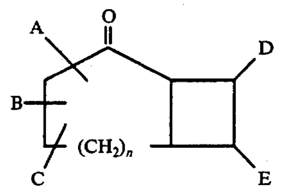

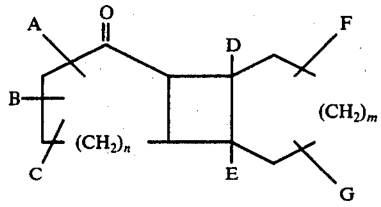

or

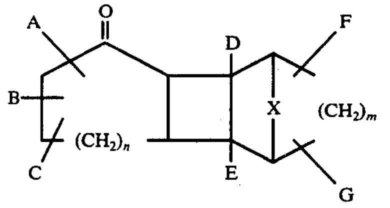

wherein *n* is an integer 0 or 1; A, B and C each independently represent hydrogen or alkyl having from 1 to 3 carbon atoms, provided that when *n* is 0 at least one of A, B or C cannot be hydrogen; D and E each independently represent hydrogen, alkyl having from 1 to 6 carbon atoms, provided that the sum of the carbon atoms in D and E does not eceed 6, alkoxy having from 1 to 5 carbon atoms or ,

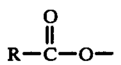

wherein R represents alkyl having from 1 to 6 carbon atoms or aryl, provided that if either D or E is alkoxy or

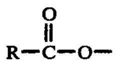

then the other substituent D or E must be hydrogen; $m$ is an integer 1 through 8; F and G represent hydrogen or alkyl having from 1 to 3 carbon atoms; X represents

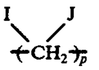

wherein $p$ is an integer 0 through 2 and I and J each independently represent hydrogen or methyl, provided that if $p$ is 0 then $m$ must be greater than 2; provided that the sum of the carbon and oxygen atoms in the compound is no greater than 23.

15. The method according to claim 14 wherein the compound used is represented by the structural formula

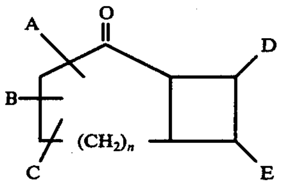

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

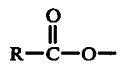

wherein R represents alkyl having from 1 to 6 carbon atoms or aryl, provided that if either D or E is alkoxy or

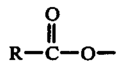

then the other substituent D or E must be hydrogen.

16. The method according to claim 14 wherein the compound used is represented by the structural formula

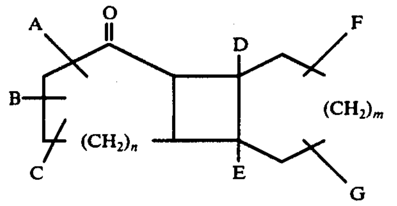

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

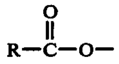

wherein R represents alkyl having from 1 to 6 carbon atoms or aryl, provided that if either D or E is alkoxy or

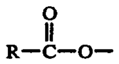

then the other substituent D or E must be hydrogen; $m$ is an integer 1 through 8; and F and G represent hydrogen or alkyl having from 1 to 3 carbon atoms.

17. The method according to claim 14 wherein the compound used is represented by the structural formula

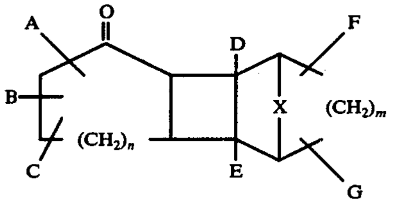

wherein $n$ is an integer 0 or 1; A, B and C each independently represent hydrogen or alkyl having from 1 to 3 carbon atoms, provided that when $n$ is 0 at least one of A, B or C cannot be hydrogen; D and E each independently represent hydrogen, alkyl having from 1 to 6 carbon atoms, provided that the sum of the carbon atoms in D and E does not exceed 6, alkoxy having from 1 to 5 carbon atoms or

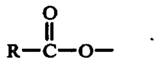

wherein R represents alkyl having from 1 to 6 carbon atoms or aryl, provided that if either D or E is alkoxy or

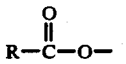

then the other substituent D or E must be hydrogen; $m$ is an integer 1 through 8; F and G represent hydrogen or alkyl having from 1 to 3 carbon atoms; X represents

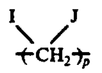

wherein $p$ is an integer 0 through 2 and I and J each independently represent hydrogen or methyl, provided that if $p$ is 0 then $m$ must be greater than 2.

18. The method according to claim 16 wherein the compound used is represented by the structural formula

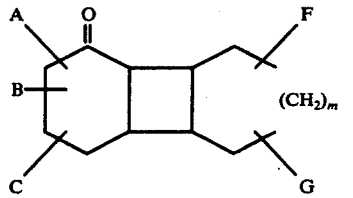

wherein A, B and C each independently represent hydrogen or alkyl having from 1 to 3 carbon atoms, $m$ is an integer 1 through 8 and F and G represent hydrogen or alkyl having from 1 to 3 carbon atoms.

19. The method according to claim 18 wherein the compound used is represented by the structural formula

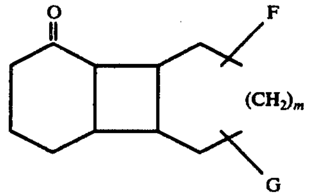

wherein F and G represent hydrogen or alkyl having from 1 to 3 carbon atoms and $m$ is an integer 1 through 8.

20. The method according to claim 18 wherein the compound used is represented by the structural formula

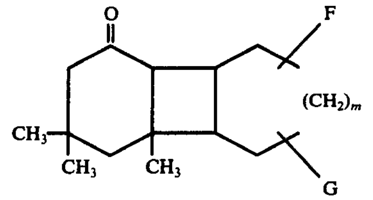

wherein F and G represent hydrogen or alkyl having from 1 to 3 carbon atoms and $m$ is an integer 1 through 8.

21. The method according to claim 14 wherein the compound used is 7-acetoxy-4,4,6-trimethylbicyclo[4.2.0]octane-2-one, 8-acetoxy-4,4,6-trimethylbicyclo[4.2.0]octane-2-one or mixtures thereof.

22. The method according to claim 14 wherein the compound used is 8-tertbutyl-4,4,6-trimethylbicyclo[4.2.0]octane-2-one.

23. The method according to claim 19 wherein the compound used is tricyclo[8.4.0.$0^{2,9}$]tetradecane-11-one.

24. The method according to claim 20 wherein the compound used is 5,5,7-trimethyltricyclo[6.4.0.$0^{2,7}$]dodecane-3-one.

25. The method according to claim 20 wherein the compound used is 1,13,13-trimethyltricyclo[8.4.0.$0^{2,9}$]-tetradecane-11-one.

26. The method according to claim 17 wherein the compound used is 6,6,8-trimethyltetracyclo[8.2.1.$0^{2,9}0^{3,8}$]tridecane-4-one.

27. A compound represented by the structural formula

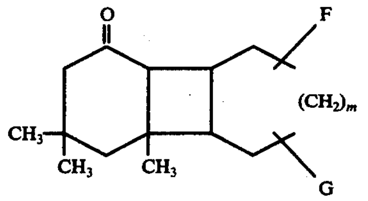

wherein $m$ is an integer from 1 through 8 and F and G represent hydrogen or alkyl having from 1 to 3 carbon atoms.

28. A compound according to claim 27 wherein $m$ is 2.

29. A compound according to claim 28 which is 5,5,7-trimethyltricyclo[6.4.0.$0^{2,7}$]dodecane-3-one.

30. A compound according to claim 27 which is 1,13,13-trimethyltricyclo[8.4.0.$0^{2,9}$]tetradecane-11-one.

* * * * *

UNITED STATES PATENT OFFICE

CERTIFICATE OF CORRECTION

PATENT NO. : 4,051,076

DATED : September 27, 1977

INVENTOR(S) : Jordan J. Bloomfield and Dennis C. Owsley

It is certified that error appears in the above-identified patent and that said Letters Patent are hereby corrected as shown below:

Column 4, line 45, after "1" please insert "-".

Column 15, line 2, "eceed" should be corrected to read -- exceed --.

Signed and Sealed this

*Seventh* Day of *February 1978*

[SEAL]

*Attest:*

RUTH C. MASON
*Attesting Officer*

LUTRELLE F. PARKER
*Acting Commissioner of Patents and Trademarks*